United States Patent [19]
Ellman et al.

[11] Patent Number: 5,695,495
[45] Date of Patent: Dec. 9, 1997

[54] ELECTROSURGICAL ELECTRODE FOR SCLEROTHERAPY

[76] Inventors: Alan G. Ellman; Jon C. Garito, both of 1135 Railroad Ave., Hewlett, N.Y. 11557

[21] Appl. No.: 560,641

[22] Filed: Nov. 20, 1995

[51] Int. Cl.$^6$ .................................................. A61B 17/39
[52] U.S. Cl. .................................................. 606/41; 606/49
[58] Field of Search ........................... 606/41, 44, 45, 606/46, 49, 50

[56] References Cited

U.S. PATENT DOCUMENTS

| | | | |
|---|---|---|---|
| 2,110,735 | 3/1938 | Marton | 606/44 |
| 3,035,580 | 5/1962 | Guiorguiev | 606/44 |
| 3,651,812 | 3/1972 | Samuels | 606/44 |
| 5,195,959 | 3/1993 | Smith | 606/49 |
| 5,403,311 | 4/1995 | Abele et al. | 606/49 |
| 5,437,664 | 8/1995 | Cohen et al. | 606/49 |

FOREIGN PATENT DOCUMENTS

| | | | |
|---|---|---|---|
| 651428 | 10/1937 | Germany | 606/49 |
| 2227415 | 8/1990 | United Kingdom | 606/44 |

*Primary Examiner*—Lee S. Cohen

[57] ABSTRACT

An electrode for use in an electrosurgical procedure for treating varicose veins. In a preferred embodiment, the electrode is characterized by a bare active sharpened tip portion at the end of a needle-shaped member capable of penetrating the vein of a patient. The vein-tissue damage is effected with the bare tip and the adjacent portions of the needle are made insulating to prevent accidental burns to the patient and to allow the physician to use these insulated parts to help position and guide the active tip portion during the surgical procedure.

10 Claims, 1 Drawing Sheet

ELECTROSURGICAL ELECTRODE FOR SCLEROTHERAPY

BACKGROUND OF THE INVENTION

Sclerotherapy involves introducing a sclerosing agent, be it physical, chemical or mechanical, into a vessel to produce sclerosis. One known method uses injectable sclerosants to promote internal damage. Many different kinds of chemical solutions have been used for this purpose, including Hypersonic Sodium Chloride as an osmotic agent, Sodium Morruhate as a detergent agent, Sodium Tetradecyl Sulfate as a detergent agent, Polilocanol as a detergent agent, Sclerodex-Dextroject as an osmotic agent, Chromated Glycerin, and Polyiodide Iodine. The first three have been approved by the FDA. Varying degrees of success have been achieved, with various side effects, including multiple treatments for best results.

Other treatments have also evolved, such a surgical stripping, a complex procedure requiring general anesthesia and a hospital stay. Lasers have also been used. The results with lasers have not been satisfactory. Suggestions have also been made for using high frequency currents for facial telangiectatic lesions, which are small varices, sometimes called spider veins. However, the techniques did not work well when applied to varicose veins on the lower extremities.

SUMMARY OF THE INVENTION

An object of the invention is an improved surgical procedure for the treatment of varicose veins.

Another object of the invention is an improved electrosurgical electrode for the electrosurgical treatment of varicose veins.

We have invented a novel electrode for use in electrosurgical sclerotherapy. This electrosurgical procedure using our novel electrode enables physicians to offer to patients a treatment that is essentially non-invasive and non-surgical, efficiently performed, easily learned by the physician and thus performed at a significantly reduced price, and requiring less patient follow-up with superior results compared to non-electrosurgical procedures.

The procedure using our novel electrode is based on superficial damage or destruction of the tissues lining the wall of the vein, causing collapse and obstruction of the vein. The electrode of the invention is uniquely configured to enable the active tip to reach and electrosurgically damage or destroy the vein lining by inserting an appropriately-sized fine needle into the vein, whereupon energizing the electrode will destroy the neighboring tissue lining with minimal damage to the surrounding tissue. The needle electrode is moved through the vein while it remains energized and then removed to determine whether the desired effect has been realized or a re-treatment may be necessary during the same patient visit.

In a preferred embodiment, our novel electrode is characterized by a bare active sharpened tip portion of a fine needle whose portions extending beyond the exposed tip are completely insulated by a thin electrically-insulating coating. A family of needle electrodes can be provided of increasing gauges to fit easily within large, medium, or small varices. Some medial and lateral fanning of the active point may be desirable while moving the needle, including preferably withdrawing the needle, to contact as much of the tissue lining the veins being treated as possible. The portions of the needle adjacent to the tip are made insulating to avoid excessive heating and to concentrate the high frequency currents at the needle tip. The electrosurgical procedure using the needle electrode has the important advantages of concentrating the currents causing the tissue damage at the tissue required, with minimal damage to surrounding tissue, in a relatively fast procedure, and with little pain or trauma for the patient.

It is preferred that the electrosurgical currents used be above 1.5 MHz, and preferably above 3 MHz. At these high frequencies, commonly referred to as radiosurgery, destruction is accomplished by volatilizing intracellular fluids at the point of the transmitting electrode contact which is primarily responsible for only small lateral heat spread and thus less damage to neighboring cell layers.

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

DETAILED DESCRIPTION OF THE PREFERRED EMBODIMENTS

Figure 1:
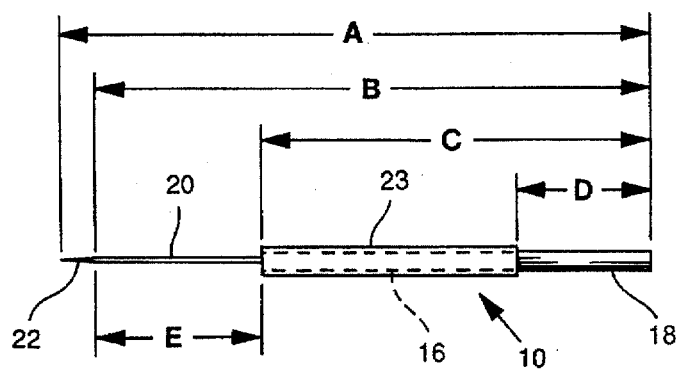
FIG. 1 is a side view of one form of electrosurgical electrode in accordance with the invention.
Figure 2:
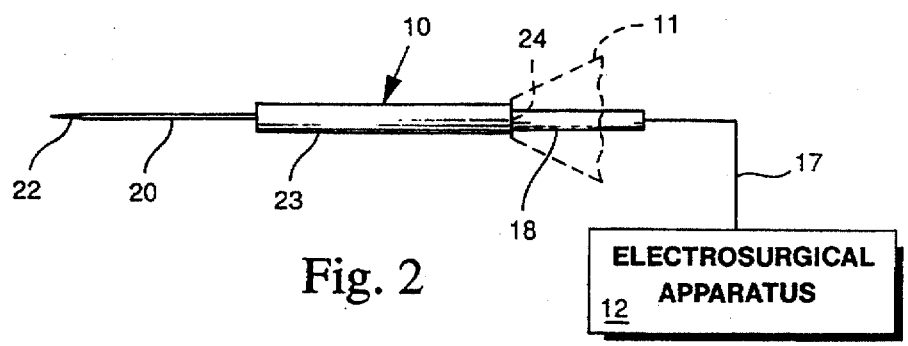
FIG. 2 is a side view of a modified form of electrode in accordance with the invention shown mounted in a conventional electrosurgical handpiece and connected to conventional electrosurgical apparatus.

FIGS. 1 and 2 illustrates preferred forms of the novel electrosurgical electrode 10. In FIG. 2, the electrode 10 of the invention is shown mounted in a standard handpiece 11 (only the front end of which is shown in phantom) which is connected in the conventional manner to conventional electrosurgical apparatus 12. As an example only, and not meant to be limiting, the handpiece can be a model H6 Surgitron handpiece available from Ellman International, Inc. of Hewlett, N.Y., and the electrosurgical apparatus can be model AAOP Surgitron FFPF available from the same supplier. The Ellman equipment is preferred due to its high operating frequency, typically at 3.8 MHz. Such handpieces 11 conventionally comprise an electrically insulating pen-like member having an electrically conductive tube (not shown) running lengthwise through it and configured to receive the bare metal shaft of the electrosurgical electrode 10. Not shown are the conventional collet type fittings at the handpiece front end to hold the metal shaft in position and to establish the desired electrical connection thereto. The opposite end of the electrically conductive tube is connected by way of a cable 17 to the electrosurgical apparatus 12. Also connected to the latter is the usual indifferent plate (not shown) which during use is in contact with the patient's body. When the electrosurgical apparatus is energized, high frequency electrosurgical currents are generated which are coupled by way of the electrically conductive tube of the handpiece to the electrode 10. The physician, in the usual way, holds the handpiece while applying the working end of the electrode to the desired area of the patient to be treated.

In accordance with the present invention, as illustrated in FIGS. 1 and 2, the electrosurgical electrode comprises a straight shaft 16, for example, of brass tubing, having at one end, the right end, a bare portion 18 to provide a good electrical connection to the handpiece, and at the opposite or working end an elongated needle 20, preferably of stainless steel, with a sharpened tip 22 capable of penetrating the skin of a patient and serving as the active electrode portion. The needle 20, which is of solid metal, is brazed or welded to the shaft end. The active tip 22 is electrically connected to the shaft 16 and any electrosurgical currents conveyed to the shaft are in turn available at the active tip 22.

A preferred embodiment has the following dimensions in inches, indicated in FIG. 1 by the letters A–D: A=2.937; B=2.819; C=1.937; D=0.687. These dimensions are not critical except for the shape and length of the sharpened tip 22. The shank 18 diameter is chosen to have a conventional diameter to fit the standard handpiece, such as 0.063 (FIG. 1) or 0.093 (FIG. 2) inches. Preferably but not essentially, the center shaft portion is covered with a thick electrically-insulating coating, such as heat-shrunk rubber tubing 23, forming a shoulder 24 (FIG. 2) which can conveniently act as a stop when the electrode 10 is inserted into the handpiece 11.

The more significant dimensions are the diameter of the needle 20, as this part extends deeply into the vein being treated, and the dimensions of the sharpened point 22. A preferred needle size is 28 or 30 gauge, approximately 0.014 to 0.012 inches in diameter, respectively, though smaller gauges may be suitable for larger veins. The needle length indicated by the dimension E can vary between about ⅜ inches for the small needles (FIG. 2) to about 1¼ inches for the larger needles (FIG. 1). The active tip portion 22, the sharpened bare point extending to the left of the dimension E, preferably has a length in the axial direction of about 0.1 inches, and can range from about 0.08–0.2 inches in length.

Figure 3:
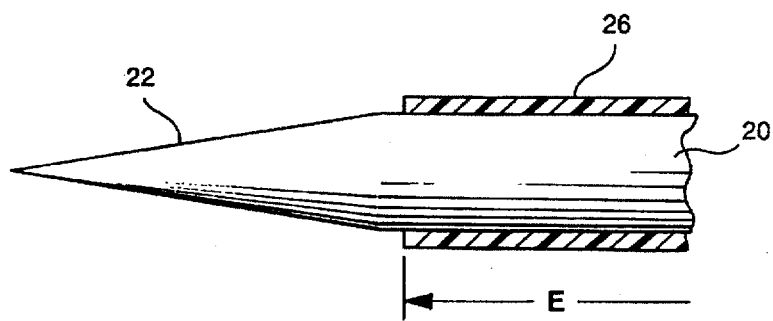
FIG. 3 is an enlarged view of the end of the electrode of FIG. 1 with the insulation shown in cross-section.

In accordance with a further feature of the invention, the portion indicated by E extending from the left end of the thick electrically-insulating coating 23 to the active sharpened tip 22 is covered with a thin coating 26 (FIG. 3) of an electrically-insulating material, which may be one of many suitable electrically-insulating plastics. Preferably, during a manufacturing step, that portion is coated with a thin electrically-insulating coating of baked Teflon, as one example. The thickness of the Teflon preferably is in the range of 0.0007 to 0.0013 inches. The insulation 26 must be thin because the needle 20 with the insulation 26 will be inserted into the vein to be treated. An enlarged view of the sharpened end of the needle 20 is shown in FIG. 3, where it will be observed that the electrically-insulating coating 26 terminates slightly to the rear of where the point 22 tapers down to a sharp point capable of penetrating the skin of a patient and entering into the patient's vein.

FIG. 1 illustrates a needle electrode for medium and large varices. FIG. 2 illustrates a smaller member of the family for small varices. In this case, the corresponding dimensions A–D are: 2.439; 2.360; 1.938; 0.687 inches.

Figure 4:
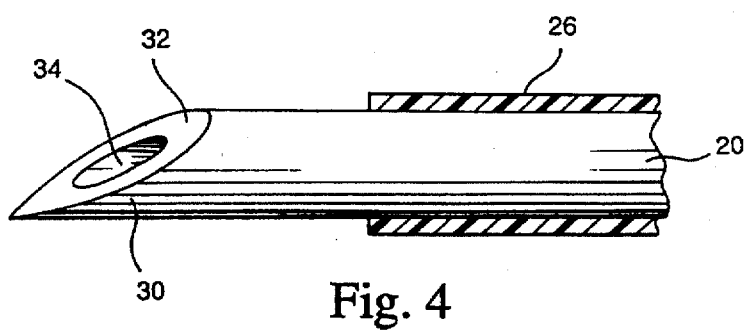
FIG. 4 is an enlarged view similar to FIG. 3 of a modified end of an electrode according to the invention.

FIG. 4 shows a modification of the active end of the needle 20. In this case, the needle end 30 is shaped as a conventional cannula, with a sharpened sloped face 32 for penetration into the patient's skin and provided with a bore 34 which extends through the needle 20. The bore 34 is not used in this sclerotherapy procedure.

The reasons for the electrode shape and protective coatings will be clearer from a description of one form of the surgical procedure. The surgeon introduces the handpiece-held electrode 10 into the vein to be treated and preferably advances it proximally as far as possible to the end of the vein. The electrosurgical apparatus 12 is then energized. The electrosurgical currents emanating only from the sharpened tip 22 will achieve tissue destruction only in the immediate surrounding area. With the current still ON, the surgeon then slowly withdraws the needle while tapping the apparatus foot switch with 1–2 second intervals. Thus, substantially the entire vein lining or short segments, if desired, can be treated with the active tip by this technique. Following withdrawal of the needle, the skin over the treated vein should be compressed to make sure no blood returns to the vessel. If blood does return, the procedure can be repeated.

The shape of the electrode 10, with a generally long, axially-oriented, main needle portion 20, makes it relatively easy to insert the electrode and reach the end of the vessel being treated. The insulating coatings 26, 23 are essential to prevent accidental burning or other tissue damage by the sides of the electrode as the instrument is manipulated through the vein passageway. Also, the inactive parts of the electrode 10 can be used by the physician to help position the active tip 22 exactly where it is needed.

With the Ellman equipment, the fully rectified current is used at a power setting of about 1–2 with the active bare tip electrode 22. There is very little trauma and pain felt by the patient.

It will also be understood that the electrode of the invention is not limited to its use for varicose veins. To those skilled in this art, there will certainly be other uses for this novel electrode that provides an active sharpened tip arranged in-line to the shaft, with the adjacent electrode sections coated with insulating material for accurately guiding and controlling the position of the active tip during a tissue damaging electrosurgical procedure.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. An electrosurgical electrode for electrosurgical sclerotherapy, comprising:
   (a) an electrically-conductive shaft member having a first end for receiving electrosurgical currents and a second end.
   (b) said second end having a needle-shaped portion terminating in an active, electrically-conductive, tip portion,
   (c) said active tip portion being a sharpened point capable of penetrating the skin of a patient and exposed electrically for applying electrosurgical currents when said shaft member is connected to a source of electrosurgical currents,
   (d) said sharpened point having a length of about 0.08–0.2 inches, and a diameter of about 0.012–0.014 inches and being configured to allow a physician to advance the sharpened point proximally into a vein to be treated of the patient,
   (e) portions of said needle-shaped portion adjacent said active tip portion being electrically-insulating to prevent contact and passage of electrosurgical currents to adjacent or surrounding tissues.

2. The electrosurgical electrode as claimed in claim 1, wherein the active tip portion extends substantially in-line with the shaft member.

3. An electrosurgical electrode as claimed in claim 2, wherein the needle-shaped portion has a length of about ⅜–1¼ inches.

4. An electrosurgical electrode as claimed in claim 1, wherein the shaft member is coated with a first electrically-insulating coating at about its center, and the needle-shaped portion is coated with a second electrically-insulating coating that is thinner than the thickness of the first coating up to the active tip portion.

5. An electrosurgical electrode as claimed in claim 4, wherein the second coating has a thickness between about 0.0007 and 0.0013 inches.

6. The combination of claim 1 with electrosurgical apparatus for generating electrosurgical currents at a frequency exceeding 1.5 MHz, said electrosurgical apparatus being connected to the first end of the shaft member.

7. A surgical procedure for treating varicose veins of a patient, comprising the steps:

(a) providing electrosurgical apparatus capable of supplying electrosurgical currents and connected to a handpiece holding an electrosurgical electrode, said electrosurgical electrode, comprising:
  (i) an electrically-conductive shaft member having a first end for receiving electrosurgical currents and a second end,
  (ii) said second end having a needle-shaped portion terminating in an active, electrically-conductive, tip portion,
  (iii) said active tip portion being a sharpened point exposed electrically for applying electrosurgical currents when said shaft member is connected to a source of electrosurgical currents.
  (iv) said sharpened point being capable of penetrating the skin of a patient and being configured to allow a physician to advance the sharpened point proximally into a vein to be treated of the patient,
  (v) portions of said needle-shaped portion adjacent said sharpened point being electrically-insulating to prevent contact and passage of electrosurgical currents to adjacent or surrounding tissues, (b) penetrating the skin of a patient and advancing the electrode proximally into the vein to be treated of the patient.

(c) activating the electrosurgical apparatus until the vein lining adjacent the active tip portion is damaged.

8. The procedure of claim 7, wherein the electrosurgical currents are at a frequency exceeding 1.5 MHz.

9. The procedure of claim 7, wherein the sharpened point has a length of about 0.08–0.2 inches, and a diameter of about 0.012–0.014 inches.

10. The procedure of claim 7, further comprising the step of:

(d) following step (c), slowly withdrawing the active tip portion from the vein while activating the electrosurgical apparatus to damage further segments of the vein lining.

* * * * *